Nov. 14, 1933. V. G. LUCAS Plant Pat. 81
PLANT
Filed Nov. 24, 1931
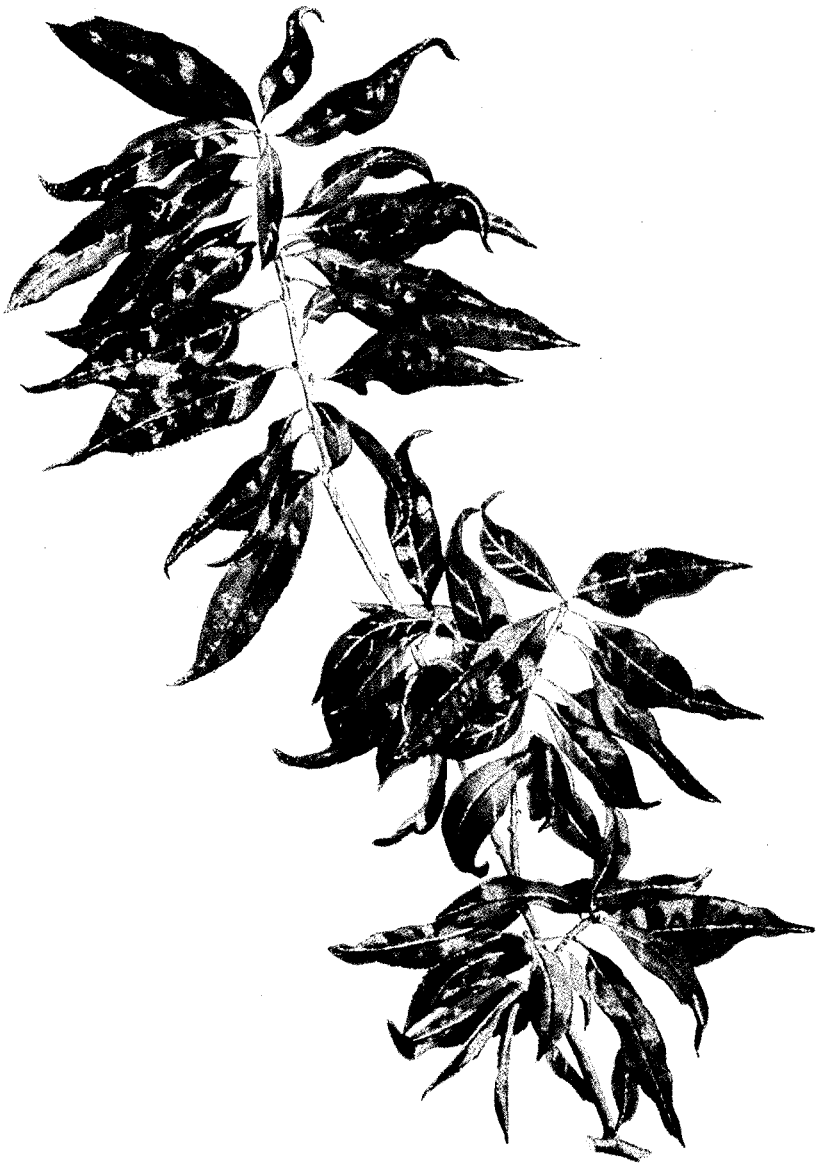
Inventor:
Vincent G. Lucas
By N. P. Litzenberg
Atty.

Patented Nov. 14, 1933

Plant Pat. 81

UNITED STATES PATENT OFFICE

81

PLANT

Vincent G. Lucas, Ontario, Calif., assignor to Lucas Ranching Co., Cucamonga, Calif., a corporation of California Application November 24, 1931
Serial No. 577,024

1 Claim. (Cl. 47—59)

My invention or discovery relates to improvements in peach trees or plants of an improved variety, the tree or plant of which will bear more certainly, and is not subject to delayed foliation, and the fruit of which will keep better in cold storage.

This plant originated in a grove of budded Lovell peach trees, planted several years ago. The original seedlings were budded with buds taken from Lovell peach trees. These grew to maturity and the major part of the grove remains. This particular tree died as a result of disease or injury, but the roots of the original seedling lived and a sprout or shoot was discovered growing from this original seedling at a point about level with the surface of the soil, or where the roots unite to form the head. The upper part of the tree, that is, that which had been budded into the seedling, was dead. This shoot was allowed to remain and by the fall of 1930 had grown into a small tree with a trunk having a diameter of about two and one-half inches. The crop of fruit beginning to ripen on this tree was of a good quality, and indicated a highly desirable new variety. This peach is of the red freestone type, nearly round, with a yellowish skin, in which red predominates as it ripens. The suture is shallow, and the tip at the apex is small and sometimes hardly noticeable. The flesh is firm and has a dark red center, with deep indentations in the pit, and the fruit has exceptionally good keeping qualities. This peach is a late ripening variety.

A distinguishing characteristic of this plant or tree is that it is not subject to delayed foliation. This has been particularly demonstrated this year of 1931, which has been one of the worst years for delayed foliation. Observation the past two years has shown that the leaves and blossoms come out vigorously and simultaneously, while, both in 1930 and 1931, and particularly in the year 1931, other varieties of late freestone type failed to come out properly in the warm valley climate of Southern California, the blossoms coming first, but owing to the condition of the sap, the blossoms did not have sufficient strength, and fell off, with the result that the crop was either light or a total failure, and the leaves did not follow the blossoms for a month or six weeks. But with this newly discovered plant it was different. The blossoms came out vigorously and the leaves followed soon thereafter, and a bountiful crop of fruit was gathered both years. In fact the fruit had to be thinned both years.

Buds from this tree have been used to bud other trees and the largest of these are now between two and three feet in height.

The drawing submitted illustrates a twig of the tree in full leaf. It grew up from the root stock and probably represents a hybrid between the variety used as stock and some other variety with which it may have been pollinated.

In comparison with other late ripening varieties of peach, this particular fruit is better flavored, more juicy, and has better keeping qualities in storage. A marked difference in the tree is that the growth of the limbs is moderately slender and open, and the leaves are narrower and more slender, and are also of a lighter green in color.

I claim:

A peach tree, as described, characterized by its early leafing, heavy bearing tendency, and late ripening of its fruit which is better flavored, more juicy, has better keeping qualities, and an attractive color, shape and size.

VINCENT G. LUCAS.